United States Patent [19]

Breuer et al.

[11] 4,151,739

[45] May 1, 1979

[54] METHOD FOR CHECKING GAS ANALYSIS DEVICES

[75] Inventors: Wolfram Breuer; Wolf-Jürgen Becker, both of Leverkusen; Jacques Deprez, Frechen; Eckard Drope, Cologne; Karl-Heinz Kaufmann, Langenfeld-Immigrath; Kurt Schreckling, Leverkusen, all of Fed. Rep. of Germany

[73] Assignee: Bayer Aktiengesellschaft, Leverkusen, Fed. Rep. of Germany

[21] Appl. No.: 791,125

[22] Filed: Apr. 25, 1977

[30] Foreign Application Priority Data

May 15, 1976 [DE] Fed. Rep. of Germany ....... 2621677

[51] Int. Cl.² .................... G01N 7/00; G01N 27/46
[52] U.S. Cl. ................................ 73/1 G; 204/1 T; 204/195 R; 204/195 P
[58] Field of Search ............. 204/1 T, 1 Y, 1 P, 1 S, 204/1 B, 195 R, 195 P; 73/1 G; 324/29; 23/232 R, 232 E

[56] References Cited

U.S. PATENT DOCUMENTS

| 3,180,132 | 4/1965 | Robinson et al. | 73/1 G |
| 3,607,073 | 9/1971 | Stamm | 23/232 R X |
| 3,888,112 | 6/1975 | Leeuw et al. | 73/1 G |
| 3,966,411 | 6/1976 | Ross et al. | 23/232 E X |
| 3,969,209 | 7/1976 | Mueller | 204/195 R |
| 3,975,947 | 8/1976 | Kruishoop | 73/1 G X |

*Primary Examiner*—G. L. Kaplan
*Attorney, Agent, or Firm*—Sprung, Felfe, Horn, Lynch & Kramer

[57] ABSTRACT

A method for checking gas analysis devices in respect of their sensitivity and their response and regeneration behaviour with respect to time, wherein a reproducible quantity of the measurement component is produced at a predetermined production rate, for a period of time which is guided entirely or at a constant proportion as a concentration pulse to the measurement element of the gas analysis device. For the production of the measurement component a chemical or electro-chemical reaction or even a thermal reaction is used. The time interval can then be conveniently controlled. A decisive advantage with toxic measurement components is that the gas production takes place in all cases for only a short time during the test procedure.

11 Claims, 6 Drawing Figures

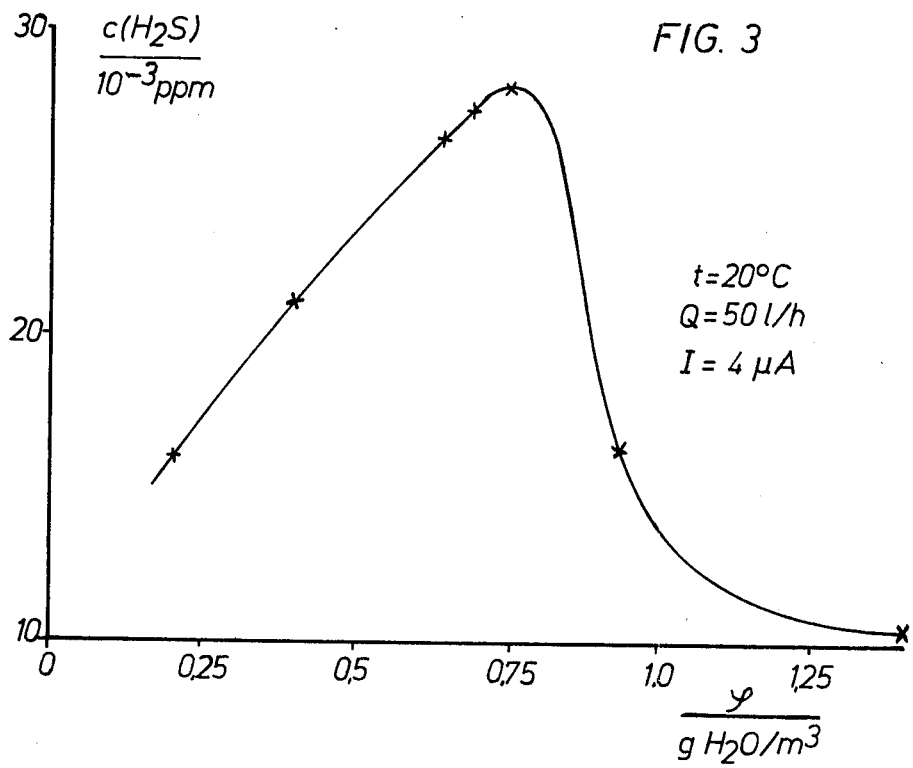
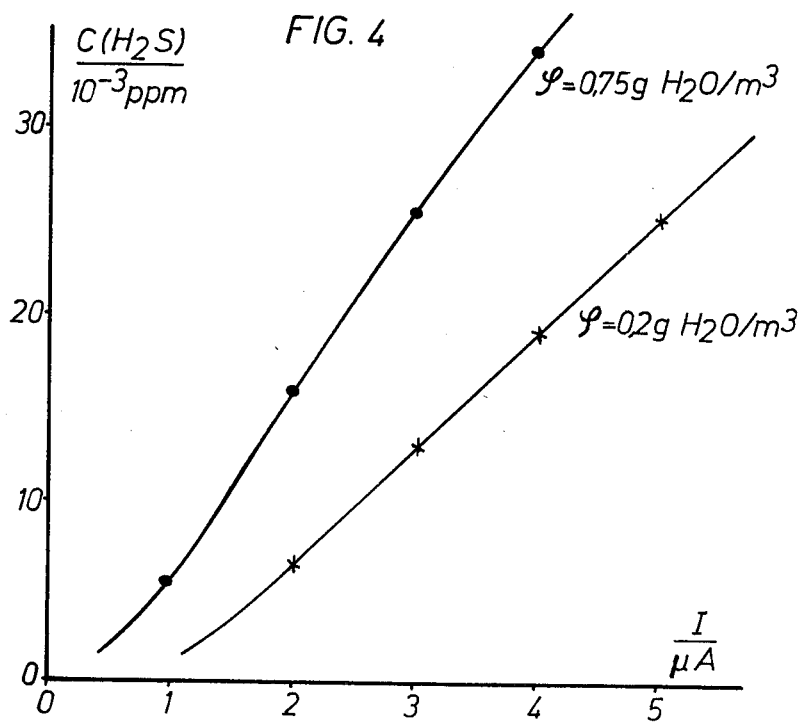

METHOD FOR CHECKING GAS ANALYSIS DEVICES

The invention relates to a method and apparatus for checking gas analysis devices with respect to their sensitivity and their response and regeneration behaviour with respect to time.

A regular function check on automatic gas analysis devices is necessary because of their high susceptibility to faults. This is frequently carried out manually. Both in automatic measurement grids as are frequently constructed today for emission monitoring and also for process monitoring in the chemical industry and particularly in ambient air monitoring in endangered work places, the requirements for a trouble-free and regular function check of the analysis device must be met. The same requirements must be set in respect of reliability and operator convenience as are already realised in computer controlled remote control systems and as are necessary for their meaningful use. In such a closed fully automatic chain

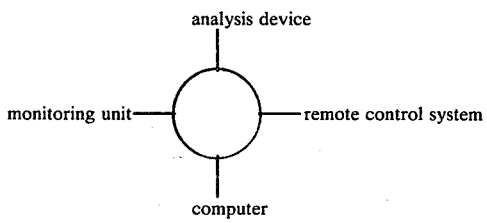

today the monitoring unit is the weak link. The function check of the analysis device is generally effected by means of a calibration gas, which is given off by a calibration point continuously by the dilution or permeation principle. These methods are very complex, and require relatively large stocks of the measurement component, which for reasons of toxicity is frequently undesirable and in addition they are very slow. To obtain relevant information, the operation of the analysis device must be interrupted for an objectionably long time. During this time the analysis device cannot fulfil its actual function. This operation interruption cannot be tolerated if the device is for example used for control or alarm purposes. In the case of the diffusion measurement head in increasing use for ambient air monitoring based on electro-chemical measurement cells or semiconductor measurement cells, automatic function checking with the hitherto conventional methods is in principle impossible.

Function checking is intended to mean that the gas analysis device can be examined simultaneously at least in respect of its sensitivity and its response and regeneration behaviour with respect to time. The method is intended also to be suitable for gas analysis devices in which the measurement gas is guided past the measurement element (through-flow measurement element) in a continuous flow, and also for devices in which the measurement component passes by diffusion to the measurement element (diffusion measurement element). Since toxic gases are frequently used, for safety reasons it is necessary that in principle large stocks of the measurement gas components are not present in the containers (e.g. gas cartridges). In addition it is important that the function check can be tripped automatically by the computer via the remote control system and evaluated.

According to the invention there is provided a method for checking gas analysis devices with respect to their sensitivity and their response and regeneration behaviour with respect to time, wherein in a time interval $\Delta t_E$ at a predetermined production rate $m_E(t)$, a reproducible quantity $$M_E = \int_{t_E}^{t_E + \Delta t_E} m_E(t)dt$$

of the measurement component is produced, either a constant proportion or all of which is guided as a concentration pulse to the measurement element of the gas analysis device.

A concentration pulse is taken in analogy with the pulse in mechanics to mean a quantity of the measurement component which within time $\Delta t_M$ acts on the measurement element, which is small in relation to the follow-up time $\tau_{95}$ (95% value) of the gas analysis device. In practice the range used is $\Delta t_M \leq 0.1\tau_{95}$. The concentration pulse arises either directly through the mechanism chosen for the gas production or is produced by special auxiliary agents from a prepared quantity.

According to a particular embodiment of the invention, the quantity $M_E$ is produced by a chemical reaction which is spontaneously induced and then terminated after a predetermined time interval $\Delta t_E$.

Another embodiment is characterised in that the quantity $M_E$ is released by the brief opening of a reservoir filled with the measurement component. Both methods can also be combined.

Particularly suitable for this method are reactions in which the reagents are brought into contact with one another momentarily.

However, for the method according to the invention an electro-chemical reaction with an electrolytic decomposition is preferably used. The beginning and end of the reaction can then be controlled particularly easily by closing or opening an electrical contact. The quantity produced of the measurement component can then be calculated from the quantity of electrical energy supplied. Alternatively the chemical reaction used to produce the quantity $M_E$ can be controlled by a thermal reaction. A further alternative is that the chemical reaction is controlled by an electrical discharge. In addition, photo-chemical reactions are suitable for the method according to the invention. By means of momentary radiation, e.g. with ultra-violet light, a series of reactions can be conveniently controlled.

Various methods can be used to produce the concentration pulse. Methods which have proved themselves include mechanical compression, the addition of propellant, or a thermal expansion in which the gas quantity produced is compressed through an aperture between the place of gas production and the measurement element. In the case of gas analysis devices based on through flow measurement cells, the quantity produced is usefully injected into the inlet pipe of the measurement cell. In the case of devices based on diffusion measurement heads, the concentration impulse is advantageously directed straight at the measurement head.

Refinements of the invention and methods for the production of special measurement gas components are described in the sub-claims.

The method according to the invention permits a very rapid function check with high information value. The simultaneous checking of sensitivity and time behaviour of the analysis device is particularly important when the time behaviour of the analysis device goes into the evaluation of the measurement result. This is the case:
1. in the correlation of emission measurements,
2. in process regulation,
3. in alarm systems in gas endangered rooms.

Point 1

As rapidly altering concentrations of different components in the air can only be correlated when the time behaviour of the different gas trace analysis units is known, the running up and regeneration time of the devices must be continuously checked.

Point 2

Frequently, control algorithms cannot be used or found, because the varying time behaviour of the analysis device cannot be monitored. To optimise the control algorithm a regular checking of the time behaviour of the analysis devices is necessary.

Point 3

The time and regeneration behaviour of the analysis device (warning device) is here of essential significance.

The regular monitoring of the time behaviour is therefore indispensable.

A further important advantage of the monitoring of gas analysis devices according to the invention is that the test gases in general can be produced with a small and manageable apparatus. In particular using an electro-chemical, photo-chemical or thermal decomposition reaction, reproducible quantities can simply be produced, with a proportional relationship generally existing between the electric current or heat energy applied and the gas quantity produced. Using these methods it is possible always to produce the same quantity discontinuously. The energy requirement is low. For the production of quantities in the trace range it lies in the order of magnitude of a few Watt-seconds. This permits the construction of a small manageable apparatus for the function testing. In contrast to the methods according to the state of the art, no pressurised container with the test gas is required. Thus in the case of toxic test gases, there is no danger to the personnel. In addition, the majority of the methods described hereinafter have proved themselves also for the continuous quantitative production of gas traces.

In the accompanying drawings:

FIG. 3 shows the dependence of the H$_2$S production on the water vapour content of the carrier gas;

FIG. 4 shows the dependence of the H$_2$S production on the electrolysis current;

Figure 1:
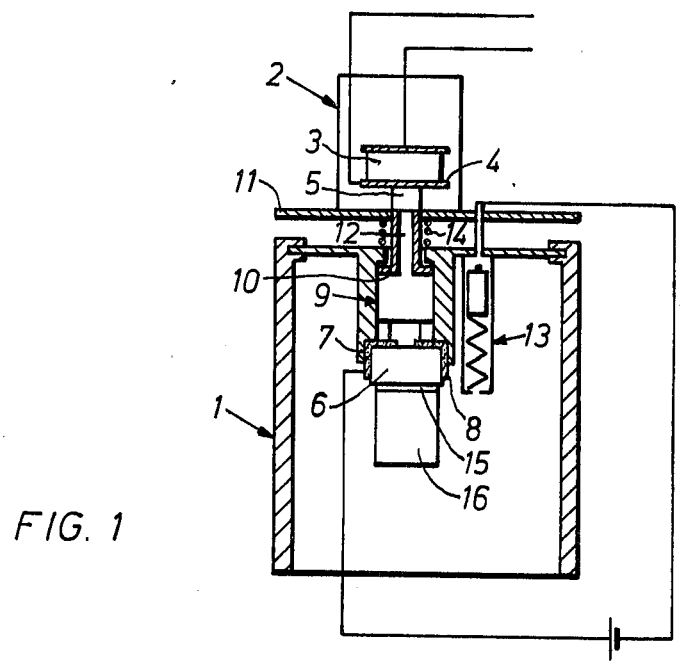
FIG. 1 shows the electro-chemical production of a quantity of gas with subsequent mechanical compression for diffusion measurement heads.

The Function Monitoring of Analysis Devices By Means of Concentration Pulses (Measurement Principle)

To test the gas analysis device, a small quantity $M_E$ of the measurement component is produced at the production rate $m_E(t)$ in the time $\Delta t_E$:

$$M_E = \int_{t_E}^{t_E + \Delta t_E} m_E(t) dt.$$

This quantity is enclosed in a volume $V_E$ and as later described is pushed out by thermal expansion or mechanical compression through an aperture or capillary. The measurement component issues from the capillary or aperture at the through-flow rate $m_K(t)$ during the time $\Delta t_K$:

$$M_K = \int_{t_K}^{t_K + \Delta t_K} m_K(t) dt \leq M_E$$

$M_K \leq M_E$ takes into account the fact that optionally only a fraction of the gas quantity $M_E$ produced is driven out through the capillary or aperture. This concentration pulse $M_K$ is then supplied to the measurement element of the gas analysis device. In this arrangement the temporal distribution $m_K(t)$ changes according to the supply mechanism to $m_M(t)$, so that the quantity $M_M \leq M_K$ is supplied to the measurement element according to the function $m_M(t)$ during the time $\Delta t_M$.

$$M_M = \int_{t_M}^{t_M + \Delta t_M} m_M(t) dt \leq M_K.$$

$M_M \leq M_K$ takes into account as in the above case the fact that optionally only a fraction of the quantity expelled from the capillary or aperture arrives at the measurement element. The measurement device then reacts to the incoming temporal distribution $m_M(t)$ of the measurement component over the time $\Delta t_A$ with its particular response function $m_A(t)$.

$$M_A = \int_{t_A}^{t_A + \Delta t_A} m_A(t) dt.$$

The response is attributed to a quantity of 1 component only which is permitted if a calibrated measuring device is used.

The transformation of the concentration pulse $$m_K(t) \xrightarrow{T} m_M(t)$$

is in practice adapted in each case to the measurement element and the measurement task. In the case of a through flow measurement cell for example, the measurement component $m_K(t)$ is injected into an inlet pipe and supplied to the measurement element by means of a flow. As a result the concentration pulse is spread. The initially almost rectangular distribution is "smeared."

In the case of a diffusion measurement cell, the measurement component $m_K(t)$ is directed straight at the cell. The transformation is therefore identical.

In practice the function monitoring of gas analysis devices is effected according to the above described method in such a way that the indication $m_A(t)$ produced by one concentration pulse is in each case compared with the preceding indication. As long as each concentration pulse produces the same indication $m_A(t)$, the device is in order. However if the indication $m_A(t)$ changes with the $i$th function check to $m_A^i(t)$, then a function fault of the measurement device can be concluded from this change. The following cases can be simply interpreted:

1. The evaluation of the maximum indication $m_{Amax}$. With very short concentration pulses the sensitivity can be directly checked. If for example it is ascertained that $$m_{Amax}^i < m_{Amax}^v$$

($m_{Amax}^v$ comparative value) then it can be concluded that the sensitivity of the device has dropped.

2. The evaluation of the integral: if for example it is ascertained that $$M_A^i = \int m_A^i(t)dt < M_A^v$$

then the sensitivity of the device has dropped.

3. The evaluation of the differential. The time behaviour of the device can be checked by means of the first differential of the response curve at the turning point $$\left. \frac{dm_A}{dt} \right/ _{Wp} \quad (= \text{reversing point})$$

(a) If on the front flank of the measurement signal it is ascertained that $$\left. \frac{dm_A^i}{dt} \right/_{Wp} < \left. \frac{dm_A^v}{dt} \right/_{Wp}$$

then the running up time of the device has increased.

(b) If on the rear flank of the measurement signal it is ascertained that $$\left. \frac{dm_A^i}{dt} \right/_{Wp} < \left. \frac{dm_A^v}{dt} \right/_{Wp}$$

then the regeneration time of the device has increased.

Criteria of the type specified can be checked and interpreted by the computer. The method specified thus completes the fully automatic chain, by the computer tripping the function monitoring via the remote control system and initiating action according to the results. Only in the case of an extreme fault is manual servicing by dialogue required.

Embodiments for the production of gas concentration pulses are described in the following.

1. Production of Gas Traces by a Chemical Reaction Which is Controlled by the External Pressure p as a State Variable In systems composed of several reactants the state depends apart from the pressure and temperature on the numbers of moles of all the reactants present. During the course of the reaction the numbers of moles change constantly until the end state is achieved. According to the law of mass action, K is designated as a thermodynamic equilibrium constant of the reaction:

$$\nu_A A + \nu_B B = \ldots \rightleftharpoons \nu_C C = \nu_D D + \ldots$$

$$K = \frac{[a_C]^{\nu_C} [a_D]^{\nu_D} \ldots}{[a_A]^{\nu_A} [a_B]^{\nu_B} \ldots}$$

in which $\sigma$ represents the equivalence numbers and a the equilibrium activity.

If a reactant D is present as a gas, then its concentration in the liquid corresponds according to the Henry-Dalton law to the gas pressure over the mixture. In a closed system, the pressure increases markedly when the gas being produced is only slightly soluble in the liquid phase. With increasing pressure the solubility of the gas increases until its concentration in the solution has reached the equilibrium concentration corresponding to the law of mass action. At that point no further chemical reaction can take place. The pressure p as a state variable determines the release of the quantity of gas. In order to transform this quantity into a concentration pulse, the auxiliary agents described further below are used.

In an open system the gas is able to escape, so that its concentration in the liquid remains low. As a result of the stoichiometric laws, the changes in the numbers of moles of the reactants are determined by the change of the remaining reactants. On reaching equilibrium, only small quantities of the starting reaction partners A and B are finally present, i.e. the reaction is practically completely concluded. By the appropriate selection of the quantities of the reactants A and B, the quantity of the test gas produced can be varied within wide limits.

The two methods mentioned above can be combined. By continuous or discontinuous regulation of the gas removal from an otherwise closed system, the closed system can be converted into an open system, so that in it a chemical reaction takes place as required and as a result a desired quantity of gas is released.

In practice, the release of the quantity of gas can be achieved by the brief opening of a valve, as a result of which the equilibrium state of the system is temporarily disturbed. The stoichiometric reaction to restore the equilibrium then corresponds to the gas quantity $M_E$ given off. This method is described with reference to the known Scheele reaction. In this reaction chlorine is produced by the oxidation of HCl with $MnO_2$. In this process chlorine and momentarily MnO are formed. Manganese oxide (MnO) then reacts with HCl to form $MnCl_2$.

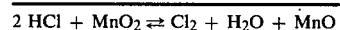
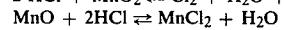
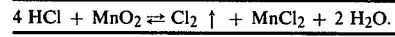

2 HCl + $MnO_2$ ⇌ $Cl_2$ + $H_2O$ + MnO
MnO + 2HCl ⇌ $MnCl_2$ + $H_2O$

4 HCl + $MnO_2$ ⇌ $Cl_2$ ↑ + $MnCl_2$ + 2 $H_2O$.

If this reaction is conducted in an open system, then a quantity is produced according to the stoichiometric conversion of the reactants. However if the reaction takes place in a closed container, the pressure rises considerably as a result of $Cl_2$ production and so does the solubility of the chlorine in the liquid phase until the reaction is stopped in the state of equilibrium. If the closed container is provided with a valve, then the reaction can be restarted by the brief opening of the valve.

2. The Production of the Quantity of Gas by a Chemical Reaction, in Which Two Reactants are Momentarily Brought into Contact with One Another A defined quantity of chlorine can, for example, be produced by briefly guiding HCl vapours over an oxidation mass of manganese IV-oxide and potassium bisulphate. The manganese IV-oxide and potassium bisulphate are in this arrangement usefully applied onto ceramic granulate as a support. The reaction takes place as follows:

$$2 HCl + MnO_2 \rightleftarrows Cl_2 \uparrow + H_2O + MnO$$
$$MnO + 2 KHSO_4 \rightleftarrows MnSO_4 + H_2O$$

$$2 HCl + MnO_2 + 2 KHSO_4 \rightleftarrows Cl_2 \uparrow + MnSO_4 + K_2SO_4 + 2H_2O.$$

In this way any desired quantity of chlorine can be produced during a specific time $\Delta t_E$. $\Delta t_E$ is simply determined by the passing-over time.

3. The Production of a Concentration Pulse by Means of Electrolytic Decomposition Quantities of gas for the method according to the invention can be produced particularly conveniently by electrolytic decomposition. FIG. 1 shows schematically a suitable apparatus. The measurement element 2 of the gas analysis device is located on the test gas generator 1. The measurement element 2 is here an electro-chemical diffusion measurement cell as for example described in German Offenlegungsschrift No. 2,436,261. FIG. 1 indicates only the electrolyte 3 of the cell with the relevant electrodes. The three phase boundary 4 responsible for the measurement effect is connected via a diaphragm 5 to the test gas generator 1. The diaphragm 5 works simultaneously as an aperture for the gas input.

The main component of the test gas generator 1 is the electrolyte 6 with the electrodes 7 and 8. By applying a voltage to the electrodes 7 and 8, an electrolytic decomposition is produced, whereby the desired quantity of gas is produced. To produce a concentration pulse, a cylinder 9 is arranged above the electrolyte cell. 6. A piston 10 is connected to the upper sealing plate 11 of the test gas generator. By depressing the sealing plate 11, the piston 10 also moves downwards so that the quantity of gas located above the electrolyte 6 is compressed to produce a concentration pulse. Through the axial bore 12 located in the piston, the concentration pulse is guided directly to the measurement element 2. In practice, a piston stroke of 2 to 5 mm with a cross-sectional area of between 0.5 and 1 cm² is sufficient.

The electrodes 7 and 8 are connected via a switch 13 to a current source. The switch 13 is coupled mechanically to the covering plate 11 in such a way that the current circuit is only closed on depressing the covering plate 11. The electrolytic decomposition therefore begins at the same moment when the measurement element 2 is placed on the test gas generator 1 and the covering plate 11 is pushed down. A pressure spring 14 ensures that the covering plate 11 returns automatically to its starting position when the plate 11 is released.

In one embodiment which has particularly proved itself, the electrolyte 6 is a hygroscopic substance. In this way, by absorbing water from the ambient air, drying out is avoided, so that the conductivity necessary for electrolysis is always present. An improvement of the life and time stability can be achieved by arranging beneath the electrolyte 6—separated by a cavity 15—an electrolyte reservoir 16 containing the same electrolyte substance. The reservoir 16 is subject to a diffusion interaction with the electrolyte 6 via the short cavity 15 (approximately 2 mm), so that the water content of the generator electrolyte 6 remains practically constant as a result of the self-adjusting diffusion equilibrium. The reservoir function 16 comes into effect both with excessively dry and excessively humid climates. In the latter case, the electrolyte 6 in communication with the ambient air gives off its excess water content by diffusion to the reservoir 16.

A suitable hygroscopic substance is for example potassium bisulphate. Particular compositions based on this substance are described further below.

In particular in the production of traces of hydrogen sulphide and chlorine it has been found that the production rate is greatly dependent on the relative humidity of the air. In the arrangement according to FIG. 1 the electrolyte 6 can be regarded as the sediment of a saturated solution, in which the proportion of the liquid phase determines the electro-chemical property. A determining factor is the conductivity in the region of the three phase boundary between electrolyte, electrode and gas chamber. Optimum conditions in the liquid phase are present when the partial vapour pressure of the water in the gas phase is equal to the pressure in the liquid phase. This can be achieved by the gas phase being adjusted to the desired water vapour pressure by a receiver containing the saturated solution of the electrolyte or by the electrolyte being surrounded by a reservoir of the same solution.

Instead of mechanical compression according to FIG. 1 to produce the concentration pulse, a propellent can also be used. This variant is particularly suitable for through-flow measurement cells, in which the gas to be examined is guided in a stationary flow past the measurement element. For checking the function of gas analysis devices based on diffusion measurement cells, the above described mechanical compression or the thermal production of the concentration pulse as described below should be used.

4. The Electrolytic Production of Hydrogen Sulphide

Figure 2:
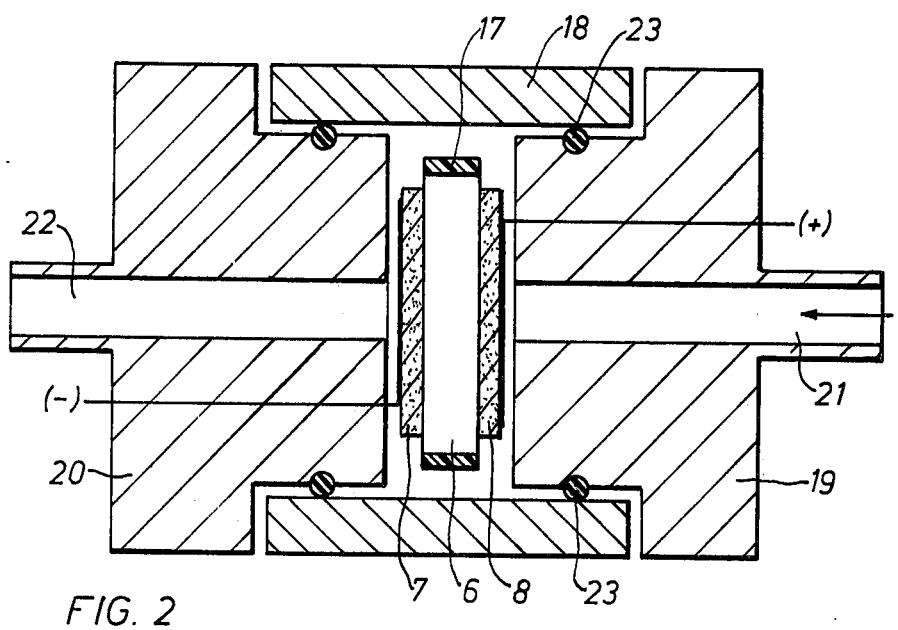
FIG. 2 shows the incorporation of a H$_2$S generator into a through-flow measurement cell.

FIG. 1 shows the function testing of a diffusion measurement cell. FIGS. 2 to 4 illustrate the production of a quantity of hydrogen sulphide for checking the function of a through flow measurement cell. The H₂S generator is here incorporated in a feed pipe to the measurement cell (see FIG. 2). The electrolyte 6 in this case consists of 50% by weight potassium bisulphate, 30% by weight sulphur and 20% by weight water. This mixture is stirred into a paste, heated to approximately 95° C. and poured into a plastics ring 17. The mixture hardens on cooling. On either side of the electrolyte electrodes 7, 8 are provided. They consist of carbon felt or carbon fabric, to provide the necessary gas permeability. On the application of a voltage to the electrodes 7, 8, hydrogen is produced at the cathode, which reacts with the sulphur contained in the electrolyte to form hydrogen sulphide:

$$2H^+ + 2e \rightarrow 2H^o$$

$$2H^o + S \rightarrow H_2S.$$

The electrolysis cell 6, 7, 8 is arranged in a cylindrical housing 18 and is held on either side by sealing caps 19 and 20.

The quantity of hydrogen sulphide produced is conveyed by means of a propellent to the measurement cell. A suitable propellent is an inert gas to which the measurement cell does not respond. The propellent flows through the bore 21 in the sealing cap 19 to the anode 8 and past the electrolyte 6 to the cathode 7. There the hydrogen sulphide issuing from the cathode is delivered with the propellent through the bore 22 in the sealing cap 20 out of the electrolysis cell. The electrode terminals are guided outwards through the sealing caps 19 and 20. The sealing caps 19 and 20 are each inserted with an O-ring 23 in gas-tight manner into the plastics housing 18.

An electrolysis cell constructed in this way was examined in respect of long term behaviour in the presence of water vapour in the propellent. It was found that:

1. The maximum hydrogen sulphide production takes place with low water vapour content in the propellent (see FIG. 3). In this case the $H_2S$ quantity produced corresponds almost to the theoretical value.
2. With permanent operation there was no exhaustion of $H_2S$ production.

The curve in FIG. 3 shows the $H_2S$ production as a function of the water vapour content of the propellant. It can be divided into two areas:

1. With increasing water vapour content up to 0.75 $g/m^3$ the $H_2S$ development increases simultaneously.
2. With a water vapour content from 0.75 $g/m^3$ there is a decreasing $H_2S$ production.

In general with increasing water vapour content the proportion of the liquid phase of the solid electrolyte becomes greater. As a result there is the danger of flooding at the critical three phase boundary between electrode 7 and electrolyte 6. Since the $H_2S$ partial pressure is dependent on the concentration of the dissolved $H_2S$, the concentration of the $H_2S$ in the gas phase initially decreases. On the other hand by the reduction of the liquid phase, an increase of the internal resistance of the electrolyte is effected. The voltage increase thus occuring leads as a result of the consequent competition reaction to a lower yield of $H_2S$. At a humidity of 0.75 g $H_2O/m^3$ and 20° C. the $H_2S$ yield is greatest. The concentration then measured is $28 \cdot 10^{-3}$ ppm (see FIG. 3). The theoretically produced concentration is calculated as $$I = \frac{m}{A \cdot t} = \frac{1}{A} \cdot Q \cdot c = 1.2 \cdot n \frac{c}{\text{ppm}} \frac{Q}{1/h} \cdot 10^{-6} A$$

in which
I = electric current,
m = mass reacted,
A = electro-chemical equivalent,
t = time,
Q = gas through-flow,
c = gas concentration and
n = number of electrons reacted (=2 for $H_2S$).

PARTICULAR EXAMPLE

For I = 4 μA there results theoretically at Q = 50 l/h a concentration $$c = \frac{I/\mu A}{1.2° n \cdot Q/(1/h)} \text{ ppm} = X \cdot 10^{-3} \, ppm.$$

the efficiency of the yield is:

$$\mu = \frac{28}{33} \cdot 100 \% = 85\%.$$

From the dependency of the $H_2S$ production on the electrolysis current (FIG. 4) there results a running up behaviour of the concentration at currents below 2 μA. This behaviour occurs even more strongly at lower humidity. At higher current the dependency is virtually linear. This indicates parallel reactions in the $H_2S$ production. Their proportion increases with lower water vapour content.

Instead of the elctrolyte mixture $H_2O + S + KHSO_4$ for the production of $H_2S$, phosphoric acid was also used. In this case the cathode consisted of a sintered carbon plate with 40% by weight of sulphur. Upon the electrolytic decomposition, hydrogen sulphide was then produced at the cathode in addition to hydrogen. The phosphoric acid electrolyte was applied to a glass frit, i.e. the electrolyte here is present in a matrix of a solid inert body.

5. The Electrolytic Production of Chlorine

As the electrolyte a mixture of potassium bisulphate $KHSO_4$ and potassium chloride KCl is used. This mixture is again highly hygroscopic and constitutes a medium strength acid of very low vapour pressure. As the electrodes again porous carbon electrodes are used. The electrolyte is produced by mixing 60% by weight $KHSO_4$, 20% by weight of KCl and 20% by weight of $H_2O$. This mixture is stirred to a paste, heated to approximately 95° C. and poured into a plastics ring. This mixture hardens by cooling.

When a voltage is applied to the electrodes, chlorine gas is produced at the anodes:

Systematic investigation regarding the influence of water vapour in the propellent were also conducted with this electrode-electrolyte-system in an arrangement according to FIG. 2. It was found that the maximum $Cl_2$ production is at a relatively high water vapour content in the propellent (approximately 85%). In permanent operation over 2 months no exhaustion of the $Cl_2$ production was detected.

With increasing humidity, the proportion of the liquid phase of the solid electrolyte becomes greater, which causes a dilution of the dissolved chlorine. On the other hand, by the reduction of the liquid phase, the contact area between electrode and electrolyte becomes smaller. This effects a current density increase at the electrodes. The voltage increase thus occurring leads to a lower chlorine yield because of competition reaction. This latter process essentially determines the $Cl_2$ yield.

6. The Electrolytic Production of Nitrogen Dioxide

As the electrolyte a mixture is used of 60% by weight potassium bisulphate $KHSO_4$, 20% by weight ammonium nitrate $NH_4NO_3$ and 20% by weight of water. This mixture is stirred to a paste, heated to approximately 95° C. and poured into a plastics ring. The mixture hardens by cooling. The design and method of functioning of the electrolysis cell corresponds to the apparatus described under 5 for the production of chlorine. When a voltage is applied to the electrodes, hydrogen is produced at the cathode and nitrogen dioxide at the anode.

7. The Electrolytic Production of Atomic Mercury Vapour

As the electrolyte a mixture is used of 75% potassium bisulphate $KHSO_4$, 5% by weight mercury-(I)-sulphate $Hg_2SO_4$ and 20% by weight of water. This mixture is stirred to a paste, heated to approximately 95° C. and poured into a plastics ring. This mixture hardens on cooling. The design and method of functioning of the electrolysis cell corresponds to the apparatus for the production of hydrogen sulphide, or chlorine. As the electrode material carbon felt is used. When a voltage is applied to the electrodes, vapour-form atomic mercury is produced at the cathode.

$$Hg^+ + e \rightarrow Hg^0.$$

The electrical power supply for the electrolytic gas production according to the Examples 4 to 7 is in all cases constructed in the same way. Either an electronic time circuit ensures that during a specific time $\Delta t_E$ a constant current flows or a capacitor is discharged through the electrolysis cell. The capacitor has for example a capacitance of 2,500 μF. The charge voltage is approximately 9 volts. The quantity of gas produced is in this case directly proportional to the charge stored in the capacitor.

8. The Production of a Phosgene Concentration Pulse

Figure 5:
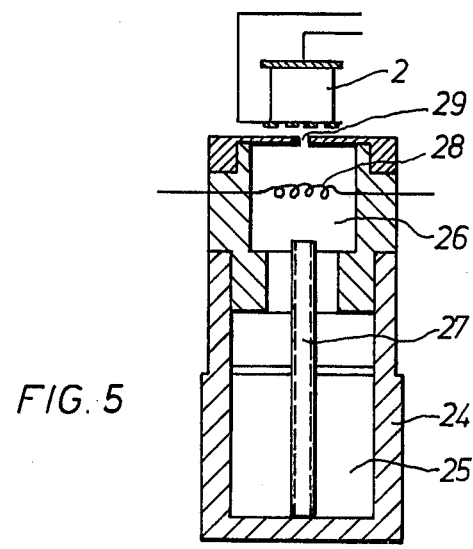
FIG. 5 shows a test gas generator for the production of a phosgene concentration pulse.

The function checking of phosgene analysers causes problems because of the high toxicity of phosgene. It is therefore an important requirement that only such small quantities of phosgene are produced during such a short time as are necessary for the testing of the analysis device. For this purpose an apparatus shown in FIG. 5 has proved itself. The phosgene generator according to FIG. 5 consists of a Teflon housing 24 with a reaction reservoir 25 and a thermal reaction chamber 26. From the reaction reservoir 25 a porous ceramic pipe 27 leads into the reaction chamber 26. The reaction reservoir 25 consists of hexachloroacetone, which together with polymethyl methacrylate forms a gel. The hexachloroacetone vapours rising through the ceramic pipe 27 are reacted in the reaction chamber 26 thermally to form phosgene. The reaction takes place on a platinum wire 28 which can be heated electrically with approximately 5 watts. Temperatures of approximately 500° C. are produced. The reaction takes place according to the equation:

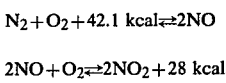

As a result of simultaneous heating in the reaction there takes place an expansion of the quantity of phosgene produced, so that a concentration pulse is generated. This concentration pulse escapes through an aperture 29 at the upper end of the reaction chamber 26. The aperture 29 has a diameter of approximately 0.3 mm. At a short interval above the aperture 29 the diffusion measurement cell 2 to be tested is arranged. It has already been described with reference to FIG. 1.

Carbon tetrachloride can be used as the reaction liquid instead of hexachloroacetone. The reaction then takes place according to the following equations:

$$CCl_4 + O_2 \text{ (air oxygen)} \rightarrow 2COCl_2 + Cl_2$$

$$CCl_4 + H_2O \text{ (air humidity)} \rightarrow COCl_2 + 2HCl.$$

To heat the heating wire 28 for a short time it is connected via a switch to a capacitor. The capacitor has for example a capacitance of 4,400 μF and is charged to a voltage of 9 volts. By means of this simple circuit current flows through the heating wire only for the short time interval $\Delta t_E$. In the discharge of this capacitor there is produced in the arrangement according to FIG. 5 for example a phosgene pulse of 20 ppm for a duration $\Delta t_E = 0.1$ s. In principle the apparatus according to FIG. 5 can also be conveniently used as a calibration gas generator for stationary tests. For this purpose the capacitor circuit is merely replaced by a circuit which delivers a constant current.

9. The Production of Nitrogen Dioxide by Means of an Electrical Discharge

In an electrical spark discharge in air, NO and $NO_2$ gas traces are produced.

$$N_2 + O_2 + 42.1 \text{ kcal} \rightleftharpoons 2NO$$

$$2NO + O_2 \rightleftharpoons 2NO_2 + 28 \text{ kcal}.$$

Figure 6:
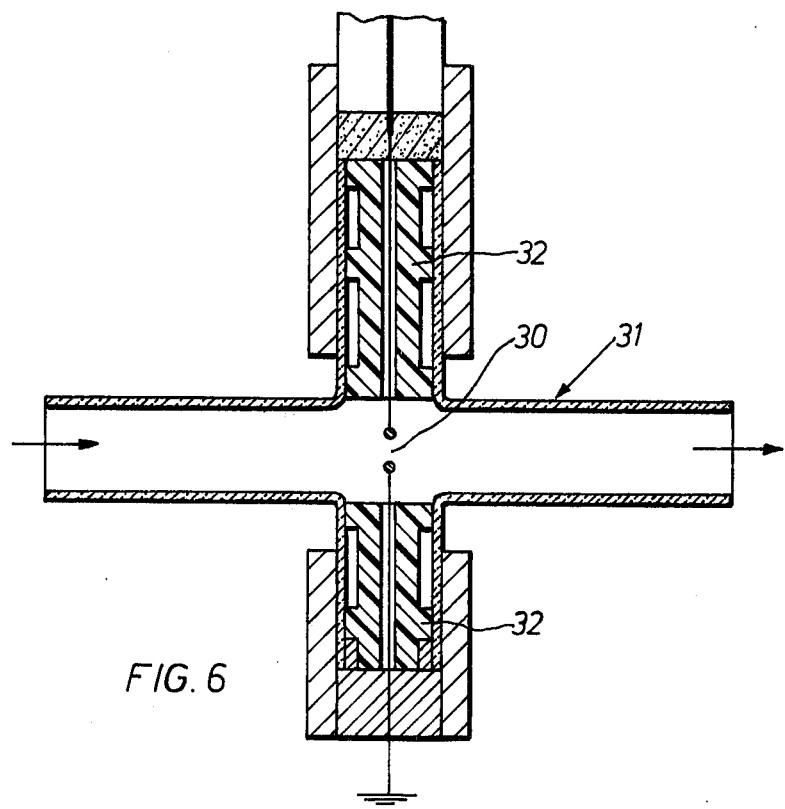
FIG. 6 shows a spark chamber for the production of NO$_X$ concentration pulses.

The apparatus for producing $NO_x$ traces by means of electric sparks is shown in FIG. 6. The spark section 30 is incorporated in a glass tube-cross piece 31. It consists of two platinum wires of 0.5 mm diameter at a distance of 2 mm. To be able to adjust the distance better, the electrodes are arranged movably (movable Teflon guides 32). To test a through-flow measurement cell the spark section is incorporated in its feed pipe. A supply device (not shown) ensures a constant air flow through the spark chamber and through flow measurement cell. By additionally incorporating an oxidation filter it is possible for the NO proportion to be quantitatively oxidised to $NO_2$.

The spark section is operated with a high voltage source (e.g. a transistor ignition system of Messrs. Bosch). With each spark there is produced a nitrogen dioxide concentration pulse which is transported to the measurement element.

In the course of miniaturization the high voltage source was replaced by a piezo-quartz. By pressure on the piezo-quartz a voltage pulse can be produced which leads to a single spark discharge. With each spark there is produced a concentration pulse of nitrogen dioxide which is transported to the measurement element. To test diffusion measurement cells the spark section is brought into the immediate vicinity of the measurement element.

The apparatus according to FIG. 6 is also suitable for permanent operation, i.e. as a calibration gas generator. In this case the high voltage source is controlled by a frequency transmitter so that sparks are produced periodically. At a spark frequency of 1.2 Hz and an electrode distance of 3 mm, for example a permanent $NO_2$ concentration is produced in the order of magnitude of 0.4 ppm.

What we claim is:

1. A method for checking gas analysis devices with respect to their known sensitivity and their known response and regeneration behavior with respect to time, wherein in a time interval $\Delta t_E$ at a predetermined production rate $m_E(t)$, a reproducible quantity $$M_E = \int_{t_E}^{t_E + \Delta t_E} m_E(t) dt$$

of the measurement component is produced and at least a constant proportion of which is conveyed to the measurement sensor of the gas analysis device, the temporal distribution of the quantity is transformed into a concentration pulse which is applied to the sensor within a period $\Delta t_M$, which is an order of magnitude shorter than the known response time of the analysis device and the response of the gas analysis device to the concentration pulse received at the sensor is evaluated.

2. A method as claimed in claim 1, wherein the quantity $M_E$ is released by the brief opening of a reservoir filled with the measurement component.

3. A method as claimed in claim 1, wherein the quantity $M_E$ is produced by a chemical reaction, which is spontaneously initiated and then terminated after the time interval $\Delta t_E$.

4. A method as claimed in claim 3, wherein the reactants for the chemical reaction are momentarily brought into contact with one another.

5. A method as claimed in claim 3, wherein the chemical reaction is controlled by an electrolytic decomposition.

6. A method as claimed in claim 3, wherein the chemical reaction is controlled by a thermal reaction.

7. A method as claimed in claim 3, wherein the chemical reaction is controlled by an electrical discharge.

8. A method as claimed in claim 3, wherein the chemical reaction is controlled by the supply of electromagnetic energy.

9. A method as claimed in claim 1 wherein the quantity of gas produced is compressed by one of mechanical compression, the addition of a propellent or thermal expansion through an aperture between the place of gas production and the measurement element.

10. A method as claimed in claim 1 wherein the quantity of gas is injected into the inlet pipe of the gas analysis device.

11. A method as claimed in claim 1 wherein the concentration pulse is directed straight at the measurement head of the gas analysis device.

* * * * *